(12) United States Patent
Latypov et al.

(10) Patent No.: US 6,312,538 B1
(45) Date of Patent: Nov. 6, 2001

(54) CHEMICAL COMPOUND SUITABLE FOR USE AS AN EXPLOSIVE, INTERMEDIATE AND METHOD FOR PREPARING THE COMPOUND

(75) Inventors: Nikolai Latypov, Tumba; Abraham Langlet, Stockholm; Ulf Wellmar, Tullinge, all of (SE)

(73) Assignee: Totalforsvarets Forskningsinstitut, Stockholm (SE)

( * ) Notice: Subject to any disclaimer, the term of this patent is extended or adjusted under 35 U.S.C. 154(b) by 0 days.

(21) Appl. No.: 09/462,479

(22) PCT Filed: Jul. 2, 1998

(86) PCT No.: PCT/SE98/01304

§ 371 Date: Jan. 18, 2000

§ 102(e) Date: Jan. 18, 2000

(87) PCT Pub. No.: WO99/03818

PCT Pub. Date: Jan. 28, 1999

(30) Foreign Application Priority Data

Jul. 16, 1997 (SE) .................................................. 9702735
Mar. 18, 1998 (SE) .................................................. 9800900

(51) Int. Cl.[7] .......................... C06B 25/35; C07C 211/22; C07C 209/76; C07D 239/02
(52) U.S. Cl. ........................ 149/92; 544/298; 548/323.5; 564/487; 564/509
(58) Field of Search .................... 564/487, 509; 544/298; 548/323.5; 149/92

(56) References Cited

U.S. PATENT DOCUMENTS 6,113,713 * 9/2000 Blomquist .............................. 149/45

OTHER PUBLICATIONS

Database CAPLUS on STN, Acc. No. 1993:559639, Baum, 'Chemistry of polynitroethane derivatives.' Report (1992), ARO–25761.5–CH–S; Order No. AD–A249264, 9 pp. Avail.: NTIS From: Gov. Rep. Annouce. Index (US) 1992, 92(16), Abstr. No. 243,310 9. (abstract), 1993.*
Database CAPLUS on STN, Acc. No. 1992: 235465, Baum et al., 'Nitration of 1,1–diamino–2,2–dinitroethylenes.' J. Org. Chem. (1992), 57(11), 3026–30. (abstract), 1992.*
Yang, C. et al, "Quantum chemical study on the effect of the substituent and the conjugated length in substituted polyeneson second order onolinear–optical coefficients", Huaxue Xuebao (1992), 50(8), 783–7.
Delpeyroux, D. et al, "A simple method for predicting crystal densities of high energy materials by molecular mechanics", Int. Annu. Conf. ICT (1993) 24th (Engergetic Materials: Insensitivity and Environmental Awareness), 74–1/74–14.
Baum, K. et al, "Synthesis and Reactions of 1,1–Diiododinitro–ethylene", J. Org. Chem., 1992, vol. 57, pp. 235–241.

* cited by examiner

Primary Examiner—Johann Richter
Assistant Examiner—Brian J. Davis
(74) Attorney, Agent, or Firm—Jacobson Holman, PLLC

(57) ABSTRACT

A new compound, 1,1-diamino-2,2-dinitroethylene suitable for use as an explosive, as well as an intermediate for preparing the compound consisting of a heterocyclic 5- or 6-ring of the general formula

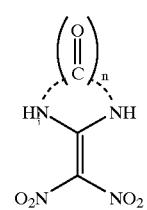

[4]

wherein n=at least 1. The compound is prepared by nitrating a heterocyclic 5- or 6-ring containing the structural element

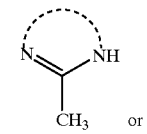

[1]

or

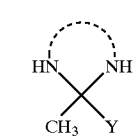

[2]

wherein Y is an alkoxy group, with a nitrating acid at a low temperature, preferably 0–30° C., and selecting the acidity of the nitrating acid for obtaining a substantial yield of a product containing the structural element

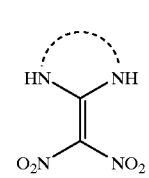

[3]

and hydrolyzing said product in an aqueous medium for separating 1,1-diamino-2,2--dinitroethylene which is recovered as a precipitate.

30 Claims, No Drawings

CHEMICAL COMPOUND SUITABLE FOR USE AS AN EXPLOSIVE, INTERMEDIATE AND METHOD FOR PREPARING THE COMPOUND

This application is a 371 of PCT/SE98/01304 filed Jul. 2, 1998.

The invention relates to a new chemical compound, viz. 1,1-diamino-2,2-dinitroethylene, which is suitable for use as an insensitive explosive. The invention also concerns an intermediate for the compound and a method for preparing the compound and the intermediate.

J. Org. Chem. 1992, 57, pp 235–241; Baum, K. et al states 1,1-diamino-2,2-dinitroethylene as an interesting target molecule in research concerning explosives since it was assumed to have interesting properties as explosive. In spite of many experiments however, it has previously not been possible to prepare the compound.

The present invention presents a method of preparing 1,1-diamino-2,2-dinitroethylene.

The invention is defined by the claims.

According to the invention, 1,1-diamino-2,2-dinitroethylene is prepared by nitrating a starting compound consisting of a heterocyclic 5- or 6-ring containing the structural element

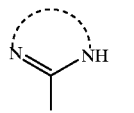

[1]

or

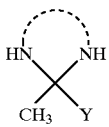

[2]

wherein Y is an alkoxy group, with a nitrating acid at a low temperature, preferably 0–30° C., and by selecting the acidity of the nitrating acid for obtaining a substantial yield of a product containing the structural element

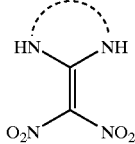

[3]

and by hydrolysing said product in an aqueous medium for separating 1,1-diamino-2,2-dinitroethylene. Y in the structural element [2] can be for instance methoxy-, ethoxy-, t-butoxy-.

The invention also relates to an intermediate, suitable for preparing 1,1-diamino-2,2-dinitroethylene, consisting of a heterocyclic 5- or 6-ring of the general formula

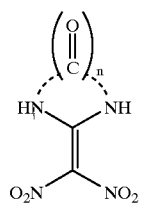

[4]

wherein n is at least 1.

The intermediate can easily be separated by hydrolysis in an aqueous medium, whereby 1,1-diamino-2,2-dinitroethylene settles out.

The intermediate is prepared according to the nitrating process included in the preparation of 1,1-diamino-2,2-dinitroethylene. In the nitration, a precipitate forms which is separated from the reaction mixture. The precipitate consists of a compound containing the structural element [3]. This primarily formed product can (depending on the starting compound) be highly unstable owing to the presence of a gem-dinitro group, $C(NO_2)_2$, on a carbon atom in the heterocyclic ring. However, this group decomposes quickly to a keto group, $C=O$, which results in a more stable and practically useful intermediate. The intermediate according to the invention contains at least one keto group on the heterocyclic ring.

As starting compound for the nitration, use can be made of 2-methyl-1,3,4-triazines of the general formula

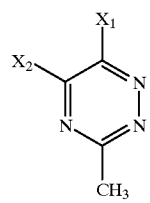

[5]

and isomers thereof, wherein $X_1$ and $X_2$ are equal or different and selected from a group consisting of —H, =O, —Cl, —Br, =N—OH, —SH, —$NH_2$ and —NH—R wherein R=alkyl group.

Other suitable starting compounds are 2-methyl-1,3,4—triazoles of the general formula

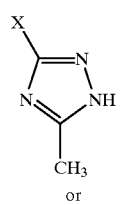

[6]

or

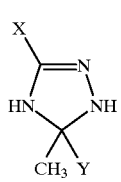

[7]

and isomers thereof, wherein Y is an alkoxy group, for instance —OMe, —OEt, —OtBu, and X is selected from a group consisting of =O, —Cl, —Br, =N—OH, —SH, —NH₂ and —NH—R wherein R=alkyl group.

Further suitable starting compounds are 2-methyl-1,3-diazines of the general formula

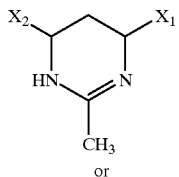

[8]

or

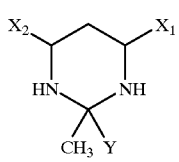

[9]

and isomers thereof, wherein Y is an alkoxy group, e.g. —OMe, OEt, OtBu, and $X_1$ and $X_2$ are equal or different and selected from a group consisting of =O, —Cl, —Br, =N—OH, —SH, —NH₂ and —NH—R wherein R=alkyl group An example of such a compound is 2-methyl-4,6-pyrimidindione

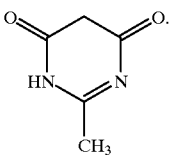

[10]

Other suitable starting compounds are 2-methyl-1,3-diazoles of the general formula

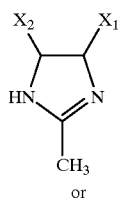

[11]

or

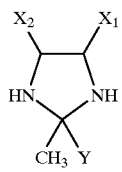

[12]

and isomers thereof, wherein Y is an alkoxy group, e.g. —OME, —OEt, —OtBu, and $X_1$ and $X_2$ are equal or different and selected from a group consisting of —H, =O, —Cl, —Br, =N—OH, —SH, —NH₂ and —NH—R wherein R=alkyl group.

Examples of such compounds are

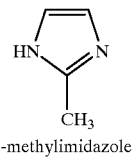

[13]

2-methylimidazole

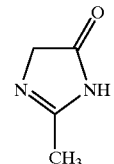

[14]

2-methyl-4(3H)-imidazolone

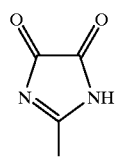

[15]

2-methyl-4,5-imidazoledione and

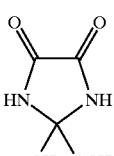

[16]

2-methoxy-2-methyl-4,5-imidazolidindione.

In the nitration use is made of a conventional nitrating system consisting of nitric acid or nitric acid in combination with another acid, i.e. a nitrating acid. In the first place nitric acid/sulphuric acid ($HNO_3/H_2SO_4$) are preferred, but other conceivable nitrating acids are nitric acid/perchloric acid ($HNO_3/HClO_4$), nitric acid/phosphoric acid ($HNO_3/H_3PO_4$), nitric acid/diphosphoric pentoxide ($HNO_3/P_2O_5$), nitric acid/acetic acid, nitric acid/acetic acid anhydride, nitric acid/trifluoroacetic acid and nitric acid/trifluoroacetic acid anhydride.

The nitration is carried out at a low temperature, e.g. 0–30° C., and with a moderate acidity of the nitrating system, e.g. 100% nitric acid and 80–100% sulphuric acid. Under these conditions, a precipitate of a product containing the structural element [3] forms in the reaction mixture. Depending on the starting compound and the used nitrating acid, temperature and acidity may need be adjusted to give an optimal yield of the product. Particularly good results have been achieved with nitric acid (100%) and sulphuric acid (90–95%), a temperature of 10–25° C., especially 15–20° C., and a molar ratio of nitric acid to substrate of 2.0–6.0:1, preferably 3.5–4.0:1.

This precipitated product can be removed from the reaction mixture, dissolved in an aqueous medium and hydrolysed, whereby the product separates 1,1-diamino-2,2-dinitroethylene, which settles out as bright yellow crystals in the aqueous medium.

The precipitated product can also, as mentioned above, be isolated as an intermediate for subsequent use for preparing 1,1-diamino-2,2-dinitroethylene. The stability of this product, however, can be limited.

1,1-diamino-2,2-dinitroethylene can also be recovered more directly without the product from the nitration first being separated by the step of adding the reaction mixture from the nitration to an aqueous medium, whereby the desired compound settles out and can be separated. In some cases, especially when the starting compound is a heterocyclic 5-ring, it may be necessary to neutralise the aqueous medium for the product containing the structural element [3] to be hydrolysed and separate 1,1-diamino-2,2-dinitroethylene.

The neutralisation can be made until the solution becomes basic, preferably at pH 8–9. The neutralisation is suitably made with an aqueous solution of ammonia, e.g. 25% ammonia solution.

The reaction will now be described in more detail, nitration of 2-methylimidazole [13] being used as a typical example.

Nitration of imidazole and 2-methylimidazole has usually been carried out with nitric acid or potassium nitrate in an aqueous sulphuric acid (70–90%) at an increased temperature (80–120° C.) and resulted in 4(5)mono-nitro derivative as the main product. According to the invention, the nitration as carried out at a low temperature, preferably 0–30° C., and especially 10–25° C. For the majority of the starting compounds, a nitrating temperature of 15–20° C. has been found to be most favorable. In addition to the temperature, the acidity of the nitrating system is important to what products are being formed.

Nitration of 2-methylimidazole at 15–25° C. with 100% $HNO_3$ in 101–105% $H_2SO_4$ mainly resulted in 2-methyl-4(5)-nitroimidazole and a certain amount of parabanic acid. Nitration with 100% $HNO_3$ in 80–100% $H_2SO_4$ gave a very small amount of 2-methyl-4(5)-nitroimidazoie, more parabanic acid and a precipitate of a gem-dinitro derivative 2-(dinitromethylene)-5,5,-dinitro-4-imidazolone of the formula

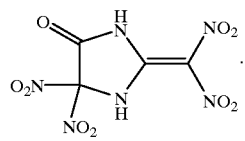

[17]

In nitration with 100% $HNO_3$ in 90% $H_2SO_4$ at 15–18° C., the gem-nitro derivative was recovered in 15% yield. The compound [17] is unstable at room temperature and decomposes within 3–5 hours while emitting $NO_x$ and forms 2-(dinitromethylene)-4,5-imidazoledione of the formula

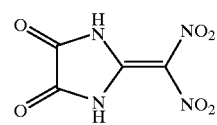

[18]

When dissolved this decomposition proceeds considerably more quickly. The acid compound [18] is thermally stable but sensitive to nucleophiles such as water and ethanol. No spectral data of the compound [17] could be obtained since the compound was very sensitive and explosive. $^{13}C$ NMR spectrum for the compound [18] resulted in the three signals 157.7, 149.4, 130.1. The compound [18] decomposed slowly in DMSO while forming parabanic acid. The compound [17] as well as [18] dissolve quickly in water (for compound [17] while forming nitrogen oxides), and in neutralisation, the ring is split and 1,1-diamino-2,2-dinitroethylene forms and settles out as bright yellow crystals. The neutralisation is preferably made until the solution becomes basic, e.g. to pH 8–9.

The separation is illustrated by the following formula for neutralisation with ammonia solution which gives dissolved ammonium oxalate besides the insoluble 1,1-diamino-2,2-dinitroethylene.

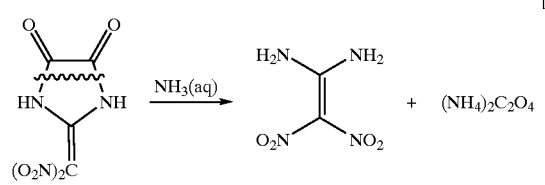

[19]

The properties of the 1,1-diamino-2,2-dinitroethylene obtained according to the invention have been examined, and the following properties and data have been established:

1.1-diamino-2.2-dinitroethylene

The compound is stable. When heated, it will decompose in two separate exothermic steps, at 220° C. and then at 275° C. The density of the crystals is 1.885 g/cm³. The explosion temperature is 215° C. It has low sensitivity to friction and impact compared with e.g. the high explosive RDX (1,3,5-triaza-1,3,5-trinitrocyclohexane). The impact sensitivity is 126 cm for 1,1-diamino-2,2,-dinitroethylene and 38 cm for RDX when using a 2 kg fall weight (BAM fall hammer). The compound is also less sensitive to friction than RDX, >350 N for 1,1-diamino-2,2-dinitroethylene and 120 N for RDX. The detonation pressure has been calculated using the program Ceeta to be 36.04 GPa and the detonation velocity to be 9040 m/s, i.e. slightly better than for RDX.

X-ray crystallographic studies of 1,1,-diamino-2,2-dinitroethylene show that the molecule in the crystal structure has bond lengths and bond angles as can be expected from this type of push-pull olefins. Some important features are, inter alia, that C=C bond distance is shortened to 1.45(1) Å; the two amino N-C bond distances, which are normally 1.40 Å for ordinary N-C (sp²) bonds, are shortened in this molecule to 1.31(1) Å and 1.32(1) Å, and the nitro N-C bond distance is 1.42(1) Å and 1.39(1) Å, respectively, as can be expected for N-C (Sp²). The carbon and nitrogen atoms in the molecule are almost coplanar with a small twist of ~5° for the nitrogen atoms. Two short intramolecular hydrogen bonds between the nitro-oxygen atoms and the amino-hydrogen atoms are present. From the absolute values of the atomic distances it is difficult to decide whether the molecular structure in the solid state corresponds to [20] or [21].

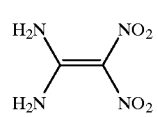

[20]

-continued

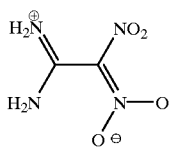
[21]

However, there are some indications in favour of [20], e.g. the nitro N-C bond distances which are as expected for N-C (Sp$^2$).

Strong intermolecular hydrogen bonds as well as van der Waal's interactions are observed in the crystal structure of the compound, which probably explains the absence of a melting point and the low solubility.

The nucleophilicity of the gem-diamino functionality in 1,1-diamino-2,2-dinitroethylene is extremely low, and 1,2-dibromomethane failed to alkylate it even in hot DMF. Under basic conditions, where the monoanion of the zwitterion according to [21] is probably present, a compound of formula

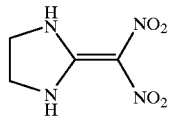
[22]

could be prepared and identified with a product previously prepared from ethylene diamine and 1,1-diiodo-2,2-dinitroethylene. See Example 7.

The reaction between 1,1-diamino-2,2-dinitroethylene and oxalyl chloride in acetonitrile under reflux easily gave the imidazole-4,5-dione [18] which after decomposition of [17] was obtained as an intermediate when nitrating 2-methylimidazole according to the invention. See Example 6.

The invention will now be described below by means of Examples:

NMR spectra were obtained using a Varian 200 MHz spectrometer. IR spectra were recorded with a Mattsson 1000 FTIR spectrophotometer. Melting points and decomposition temperatures were determined on a Mettler DSC 30. Mass spectra were recorded with a Joel D300. Elemental analyses were carried out by H. Kolbe Mikro analytisches Laboratorium, Mülheim an der Ruhr. The friction sensitivity was measured with a Julius Peter friction testing apparatus and the impact sensitivity was measured with a BAM fall hammer.

EXAMPLE 1

Nitration of 2-methylimidazole [13]

Finely ground 2-methylimidazole (4.1 g, 0.05 mole) was dissolved in concentrated sulphuric acid (40 ml, 1.84 g/cm$^3$) at 15–20° C. during vigorous stirring. At the same temperature nitric acid (8.0 ml, 1.52 g/cm$^3$) was added over a 30-min period. At the beginning of the addition, the reaction mixture became dark and then slowly turned brighter with a distinct pink coloration. After 3 h, a white precipitate of 2-(dinitromethylene)-5,5-dinitro-4-imidazolone (compound [17]) was formed, which was collected and washed several times with trifluoroacetic acid. The precipitate was dried under vacuum at 0° C. When the precipitate was allowed to stand at room temperature, it lost 28% of its weight and gave 1.7 g (yield 15%) of 2-(dinitromethylene)-4,5-imidazoledione (compound [18]).

The following data were recorded for the compound [18]:

Decomposition temperature 240° C. (10° C./min DSC). IR(KBr) 3305 (NH), 3280 (NH), 1805 (C=O), 1587, 1511, 1312, 1274, 912, 807 cm$^{-1}$. $^1$H NMR (DMSO-d$_6$) δ 11.01 ppm. $^{13}$C NMR (DMSO-d$_6$) δ 131.1,153.5, 159.8. MS m/e 202 (M$^+$). Analysis for C$_4$H$_2$N$_4$O$_6$, Calculated: C, 23.77; H, 1.0; N, 27.72. Found: C, 23.88; H. 1.25; N, 27.82.

The filtrate was diluted with water (1.5 times by weight). Neutralisation with 25% ammonia solution to pH 5–6 gave a precipitate of 2-methyl-5-nitroimidazole (0.5 g). Further adjustment of pH to 9–11 and cooling to 10° C. resulted in the precipitation of 1.5 g (20%) of the ammonium salt of the parabanic acid (as a monohydrate).

1.25 g (6.2 mmole) of the product isolated from the nitrating stage 2-(dinitromethylene)-4,5-imidazoledione (compound [18]) were dissolved in water (5 ml) and 25% ammonia solution (2 ml) was added to achieve pH 8–9. The white solid product immediately dissolved, and within a few seconds bright yellow crystals settled out (1,1-diamino-2,2-dinitroethylene). The precipitate was washed with water and dried at 50° C. to give 0.8 g (87%) of 1,1-diamino-2,2-dinitroethylene. The following data were recorded for the compound:

IR (KBr): 3417 (NH$_2$), 3315 (NH$_2$), 1638 (NH$_2$), 1530 (NO$_2$), 1400, 1356 (NO$_2$) cm$^{-1}$. $^1$H NMR (DMSO-d$_6$) δ 8.77 ppm. $^{13}$H NMR δ 128.5, 158.8; MS m/e 148 (M$^+$); Analysis for C$_2$H$_4$N$_4$O$_4$: Calculated: C, 16.22; H, 2.72; N, 37.84. Found C, 16.06; H, 2.62; N, 37.68.

EXAMPLE 2

Nitration of 2-methyl-4(3H)-imidazolone [14]

2-methyl-4(3H)-imidazolone was added in portions to a solution of nitric acid (100%, 2.0 ml) and sulphuric acid (90%, 9 ml) at 0–5° C. The clear solution was allowed to reach 15° C. during 1 h and was stirred at this temperature for an additional hour. During this period the product (compound [17]) separated as a solid, which was collected by filtration after dilution of the reaction mixture with trifluoroacetic acid (6 ml) and cooling to 5° C. The precipitate was washed with trifluoroacetic acid, dried and stored in a refrigerator. Yield 0.75 g, (27%).

In the same way as described in Example 1, the precipitate was later dissolved in water and neutralised with 25% ammonia solution, whereby 1,1-diamino-2,2-dinitroethylene settled out and was filtered off.

When storing the compound [17], it successively decomposed to compound [18], which, however, did not affect the recovery of 1,1-diamino-2,2-dinitroethylene. If the neutralisation was carried out relatively immediately after the precipitate had been isolated from the nitrating stage, the formation of nitrogen oxide could be established.

EXAMPLE 3

Nitration of 2-methyl-4,6-pyrimidindione [11]

Finely ground 2-methyl-4,5pyrimidindione (5.1 g, 0.05 mole) was dissolved in concentrated sulphuric acid (40 ml, 1.84 g/cm$^3$) at 15–20° C. during vigorous stirring. At the same temperature nitric acid (8.0 ml, 1.52 g/cm$^3$) was added over a 30-min period. After 3 h, the reaction mixture was poured into water. Within a few seconds, bright yellow crystals settled out (1,1-diamino-2,2-dinitroethylene). The precipitate were washed with water and dried at 50° C. 2.6 g 1,1-diamino-2,2-dinitroethylene was recovered (35% yield).

EXAMPLE 4

Synthesis of 2-methoxy-2-methyl-4,5-imidazolidindione [16]

The substance was found to form easily in synthesis of 2-methyl-4,5-imidizoledione. Sodium (7.7 g; 0.34 mole) was dissolved in 300 ml methanol and acetamidine hydrochloride (9.6 g; 0.10 mole) was added to the solution. The mixture was allowed to stand during stirring for 15 min, whereupon a solution of diethyloxalate (15.1 g; 0.103 mole) in 100 ml methanol was added dropwise during 3 h. The reaction mixture was treated with gaseous hydrogen chloride to achieve pH 5. A precipitate of NaCl formed and was separated by filtration, and the filtrate was concentrated under reduced pressure at 30–35° C. to 70–80 ml. A white precipitate formed, which was separated by filtration, dried at 40° C. and was found to be a mixture of an organic product and sodium chloride. After extraction with acetone in a Soxlet apparatus, the organic product was found through 1 H NMR to be a mixture of 2-methyl-4,5-imidazoledione [15] and 2-methoxy-2-methyl-4,5-imidazolidindione [16]. In recrystallisation from methanol, all 2-methyl-4,5-imidazoledione was transformed to compound [16] and gave a total of 9.6 g (64%) 2-methoxy-2-methyl-4,5-imidazolidindione. The following data were recorded for compound [16]:

Melting point=158° C. (decomposes). IR(KBr): 3249 (NH), 1755 (C=O), 1477,1427, 1388, 1176, 1124, 1047, 790, 674, 597 $cm^{-1}$. 1H NMR (DMSO-d6) $\delta$ 1.56 (s, 3H, CH3), 2.97 (s, 3H, O—CH3), 9.98 (s, 2H, NH) ppm. 13C NMR (DMSO-d6) $\delta$ 27.2, 48.2, 92.0, 160.2.

The mixture with compound [15] besides gave the following 1 H NMR signals (DMSO-d6) $\delta$ 1.50 (s, 3H, CH3), 9.65 (s, 1H, NH) ppm. Analysis for $C_5H_8N_2O_3$: Calculated: C, 41.67; H, 5.65; N, 19.30. Found: C, 41.49; H, 5.59; N, 19.44.

EXAMPLE 5

Nitration of 2-methoxy-2-methyl-4,5-imidazolidindione [16]

1.4 g (12 mmole) of the dione [16] were dissolved at 15–20° C. in 9.0 ml concentrated sulphuric acid (d=1.84) and concentrated nitric acid (1.50 ml, 36.2 mmole) was added dropwise during 5 min. The temperature was kept below 30° C. by external cooling. After 10 min, a precipitate of 2-(dinitromethylene)-4,5-imidazoledione formed. The precipitate was separated by filtration, washed with trifluoroacetic acid (3×5 ml) and dried under vacuum at room temperature. 1.48 g pure substance was recovered, corresponding to 63% yield. An analysis showed that the product was identical with compound [18].

In the same way as described in Example 1, the compound was later dissolved in water and neutralised with 25% ammonia solution, whereby 1,1-diamino-2,2-dinitroethylene settled out and was filtered off.

Examples of the Chemical Appearance of 1,1-diamino-2,2-dinitroethylene

EXAMPLE 6

1,1-diamino-2,2-dinitroethylene (148 mg, 1 mmole) was added to acetonitrile (6 ml) at 25° C. Oxalyl chloride (190 mg, 1.5 mmole) was added to the mixture during stirring, and the mixture was then kept under reflux for 2 min to give a clear solution and evolution of HCl. Concentration of the solution to about 3 ml followed by addition of diisopropylether gave the product as a white solid, which was recrystallised from toluene/acetonitrile. Yield: 170 mg (83%). The IR and mass data were identical with those for the product [18] obtained by nitration of 2-methyl imidazole.

EXAMPLE 7

Sodium hydride (96 mg, 4 mmole) was added in portions to a stirred solution of 1,1-diamino-2,2-dinitroethylene (296 mg, 2 mmole) under nitrogen in dry N,N-dimethylformamide (6.0 ml) at 25° C. When the evolution of hydrogen had ceased (5–10 min), 1,2-dibromoethane (368 mg) was added. TLC analysis showed that no product had been formed after 2 h at 25° C. The temperature was therefore successively increased, and it was found that 2 h at 115° C. was sufficient for complete alkylation. Cooling of the solution followed by addition of water containing acetic acid (0.3 ml) gave the crude product [22] which was recrystallised from toluene/diisopropylether. The melting point was measured to be 261–262° C.

What is claimed is:

1. A chemical compound suitable for use as an explosive consisting of 1,1-diamino-2,2-dinitroethylene.

2. A method of preparing the compound of claim 1, which comprises nitrating a heterocyclic 5- or 6-membered ring containing the structural element

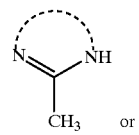

[1]

or

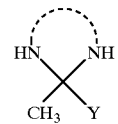

[2]

wherein Y is an alkoxy group, with a nitrating acid at a low temperature and selecting the acidity of the nitrating acid to obtain a yield of a product containing the structural element

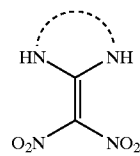

[3]

and hydrolysing said product in an aqueous medium to separate 1,1-diamino-2,2-dinitroethylene.

3. A method as claimed in claim 2, characterised by hydrolysing the product by neutralisation in the aqueous medium.

4. A method as claimed in claim 2, characterised by separating the product containing the structural element [3] from the reaction mixture as a precipitate and then hydrolysing it in an aqueous medium.

5. A method as claimed in claim 2, characterised by hydrolysing the product by mixing the reaction mixture from the nitration with an aqueous medium, and optionally neutralising said product.

6. An intermediate suitable for preparing the compound of claim 1, characterised in that it consists of a heterocyclic 5- or 6-membered ring of the general formula

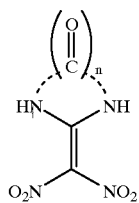

[4]

wherein n is at least 1.

7. A method of preparing an intermediate suitable for preparing the compound of claim 1, characterised by nitrating a heterocyclic 5- or 6-membered ring containing the structural element

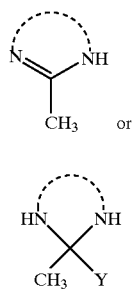

[1]

or

[2]

wherein Y is an alkoxy group, with a nitrating acid at a low temperature and selecting the acidity of the nitrating acid to obtain a yield of a product containing the structural element

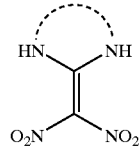

[3]

and recovering said product from the reaction mixture as a precipitate.

8. A method of preparing 1,1-diamino-2,2-dinitroethylene, which comprises hydrolysing an intermediate according to claim 6 in an aqueous medium to separate 1,1-diamino-2,2-dinitroethylene.

9. A method as claimed in claim 8, characterised by hydrolysing the intemiediate by neutralisation in the aqueous medium.

10. A method as claimed in claim 9, characterised by carrying out the neutralisation until the solution becomes basic.

11. A method as claimed in claim 9, characterised by carrying out the neutralisation with an ammonia solution.

12. A method as claimed in claim 2 or 7, characterised in that the starting compound is a heterocyclic 6-membered ring of the general formula

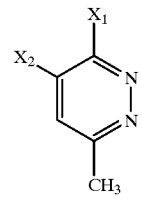

[5]

and tautomers thereof, wherein $X_1$ and $X_2$ are the same or different and selected from the group consisting of —H, =O, —Cl, —Br, =N—OH, —SH, —NH$_2$ and —NH—R wherein R is an alkyl group.

13. A method as claimed in claim 2 or 7, characterised in that the starting compound is a heterocyclic 5-membered ring of the general formula

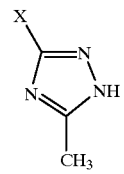

[6]

and tautomers thereof, wherein X is selected from the group consisting of =O, —Cl, —Br, =N—OH, —SH, —NH$_2$ and —NH—R wherein R is an alkyl group.

14. A method as claimed in claim 2 or 7, characterised in that the starting compound is a heterocyclic 5-membered ring of the general formula

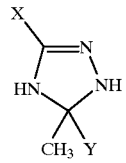

[7]

and tautomers thereof, wherein Y is an alkoxy group and X is selected from the group consisting of =O, —Cl, —Br, =N—OH, —SH, —NH$_2$ and —NH—R wherein R is an alkyl group.

15. A method as claimed in claim 2 or 7, characterised in that the starting compound is a heterocyclic 6-membered ring of the general formula

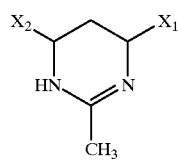

[8]

wherein $X_1$ and $X_2$ are the same or different and selected from the group consisting of =O, —Cl, —Br, =N—OH, —SH, —NH$_2$ and —NH—R wherein R is an alkyl group.

16. A method as claimed in claim 2 or 7, characterised in that the starting compound is a heterocyclic 6-membered ring of the general formula

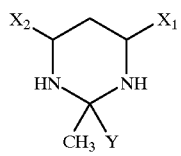

[9]

wherein Y is an alkoxy group and $X_1$ and $X_2$ are the same or different and selected from the group consisting of =O, —Cl, —Br, =N—OH, —SH, —NH$_2$ and —NH—R wherein R is an alkyl group.

17. A method as claimed in claim 2 or 7, characterised in that the starting compound is a heterocyclic 5-membered ring of the general formula

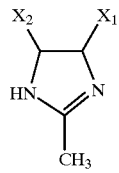

[11]

wherein $X_1$ and $X_2$ are the same or different and selected from the group consisting of —H, =O, —Cl, —Br, =N—OH, —SH, —NH$_2$ and —NH—R wherein R is an alkyl group.

18. A method as claimed in claim 2 or 7, characterised in that the starting compound is a heterocyclic 5-membered ring of the general formula

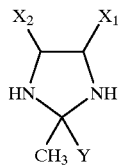

[12]

wherein Y is an alkoxy group and $X_1$ and $X_2$ are the same or different and selected from the group consisting of —H, =O, —Cl, —Br, =N—OH, —SH, —NH$_2$ and —NH—R wherein R is an alkyl group.

19. A method as claimed in claim 2 or 7, wherein the starting compound is a member selected from the group consisting of the compounds:

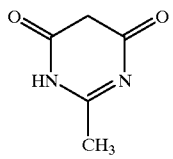

[10]

2-methyl-4,6-pyrimidindione

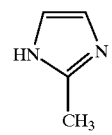

[13]

2-methylimidazole

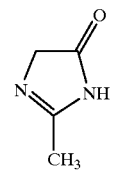

[14]

2-methyl-4(3H)-imidazolone

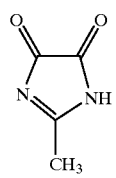

[15]

2-methyl-4,5-imidazoledione

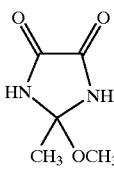

[16]

2-methoxy-2-methyl-4,5-imidazolidindione and, where appropriate, a tautomer thereof.

20. A method as claimed in claim 2 or 7, characterised in that the nitrating acid is selected from the group consisting of nitric acid (HNO$_3$), nitric acid/sulphuric acid (HNO$_3$/H$_2$SO$_4$), nitric acid/perchloric acid (HNO$_3$/HClO$_4$), nitric acid/phosphoric acid (HNO$_3$/H$_3$PO$_4$), nitric acid/diphosphoric pentoxide (HNO$_3$/P$_2$O$_5$), nitric acid/acetic acid, nitric acid/acetic acid anhydride, nitric acid/trifluoroacetic acid and nitric acid/trifluoroacetic acid anhydride.

21. A method as claimed in claim 2 or 7, wherein the nitrating acid consists of nitric acid of 100% concentration and sulphuric acid of 80–100% concentration.

22. A method as claimed in claim 21, characterised in that the molar ratio of nitric acid to starting substance is 2.0–6.0:1 in the nitration.

23. A method as claimed in claim 21, characterised by carrying out the nitration at a temperature of 10–25° C.

24. A method as claimed in claim 3, wherein the neutralisation is carried out until the solution becomes basic.

25. A method as claimed in claim 3, wherein the neutralisation is carried out to pH 8–9.

26. A method as claimed in claim 3, wherein the neutralisation is carried out with an ammonia solution.

27. A method as claimed in claim 9, wherein the neutralisation is carried out to pH 8–9.

28. A method as claimed in claim 2 or 7, wherein the nitration is carried out at a temperature of 0–30° C.

29. A method as claimed in claim 21, wherein the molar ratio of nitric acid to starting substance is 3.5–4.0:1 in the nitration.

30. A method as claimed in claim 21, wherein the nitration is carried out at a temperature of 15–20° C.

* * * * *